United States Patent [19]

Lin et al.

[11] Patent Number: 5,248,821

[45] Date of Patent: Sep. 28, 1993

[54] PROCESS FOR PREPARING POLYOXYETHYLENE AMINES WITH UREA LINKAGES

[75] Inventors: Jiang-Jen Lin, Round Rock; George P. Speranza, Austin, both of Tex.

[73] Assignee: Texaco Inc., White Plains, N.Y.

[21] Appl. No.: 846,986

[22] Filed: Mar. 9, 1992

Related U.S. Application Data

[63] Continuation of Ser. No. 78,311, Jul. 27, 1987, abandoned.

[51] Int. Cl.$^5$ .......................................... C07C 273/00
[52] U.S. Cl. ........................................ 564/55; 564/48; 564/56
[58] Field of Search ..................... 564/55, 56, 57, 59, 564/48

[56] References Cited

U.S. PATENT DOCUMENTS

| | | | |
|---|---|---|---|
| 3,654,370 | 4/1972 | Yeakey | 564/480 |
| 3,655,627 | 4/1972 | Hutzler et al. | 528/61 X |
| 4,108,842 | 8/1978 | Konig et al. | 528/61 |
| 4,485,227 | 11/1984 | Fox | 528/61 |
| 4,569,982 | 2/1986 | Grogler et al. | 528/73 |
| 4,578,447 | 3/1986 | Humphrey | 528/73 |
| 4,581,433 | 4/1986 | Potter et al. | 528/64 |
| 4,588,783 | 5/1986 | Chang | 525/374 |
| 4,604,445 | 8/1986 | Kay et al. | 528/79 X |
| 4,609,718 | 9/1986 | Bishop et al. | 528/49 |
| 4,611,043 | 9/1986 | Bruson et al. | 528/49 |
| 4,614,787 | 9/1986 | Szycker et al. | 528/75 |
| 4,689,356 | 8/1987 | Peffley et al. | 521/59 |

FOREIGN PATENT DOCUMENTS

184133 6/1986 European Pat. Off. .

OTHER PUBLICATIONS

Cunliffe et al, Polymer, Feb. 26, 1985, p. 301 only.

*Primary Examiner*—Allen J. Robinson
*Assistant Examiner*—Shailendra Kumar
*Attorney, Agent, or Firm*—James L. Bailey; Kenneth R. Priem; Cynthia L. Kendrick

[57] ABSTRACT

High molecular weight active polyoxyalkylene reaction product formed in two steps and containing urea or urethane and urea linkages are disclosed which contain as the principle reaction component, a diamine having the formula:

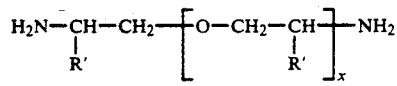

or a diol having the formula:

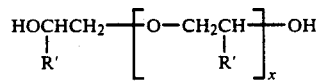

wherein R' independently represents hydrogen or methyl and x is a number having an average value of at least 1 to about 70 and a diisocyanate of the formula:

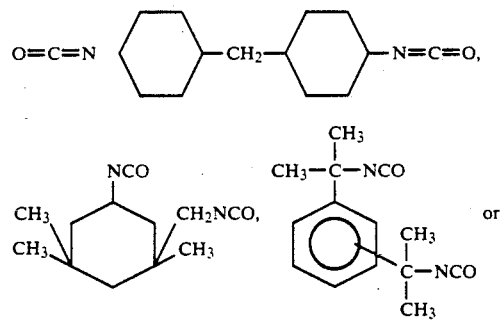

$OCN$–$(CH_2)_6$–$NCO$, and an active amine selected from the group consisting of amine terminated triethylene glycol, amine terminated tetraethylene glycol, isophorone diamine, dipropylene triamine, or diethylene triamine.

1 Claim, No Drawings

PROCESS FOR PREPARING POLYOXYETHYLENE AMINES WITH UREA LINKAGES

This application is a continuation of Ser. No. 07/078,311, filed Jul. 27, 1987 now abandoned.

FIELD OF THE INVENTION

This invention relates to various molecular weight active amines containing urea linkages. More particularly, this invention relates to the preparation of high molecular weight active amines which contain urea linkages or urethane and urea linkages. These novel active amines are prepared by contacting a reactant from the group consisting of polyoxyalkyleneamines or specified polyols with an isocyanate to form an intermediate which is reacted with active "end" amines to form novel high molecular weight amines which are very reactive. The "end" amines are polyoxyethylene diamines which are active amines in relation to polyoxypropylene diamine.

These high molecular weight active amine products can be colorless and may be used as epoxy curing agents. Those containing urethane and urea linkages are useful in the field of polymers, especially in epoxy materials for polymer concrete.

DESCRIPTION OF ART IN THE FIELD

There are references in the art which disclose the preparation of polymers containing amines. However, there does not appear to be a body of knowledge regarding the preparation of amines of high molecular weight which contain urea linkages or urethane and urea linkages.

In related copending case U.S. Pat. application Ser. No. 07/078,308 there is disclosed an aromatic amidoamine reaction product prepared by reacting an aromatic di- or tricarboxylic acid, ester or anhydride thereof with at least 2 mole equivalents of a polyoxyalkyleneamine.

In European Patent Application 0 184 133 there is disclosed a novel polyamidoamine having the formula:

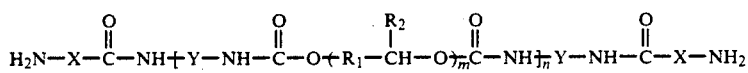

which can be used as a hardener for epoxy resins and is prepared by a two-step process wherein a —NCO terminated resin is prepared in the first step and in the second step is reacted with the polyamine. The claimed structures are derived from active aromatic diisocyanate, polyol and a polyamine, such as diethylene triamine. The physical properties of these compounds were not identified.

In U.S. Pat. No. 4,588,783 there is disclosed a curable composition comprising an amide-containing polyhydroxyethyl carbonate which is prepared by reacting an amidoamine and a cyclic organic carbonate.

In U.S. Pat. No. 4,578,447 there is disclosed a nylon-based urethane block prepolymer suitable for reaction injection molding when reacted with an anionic catalyst comprising a monovalent metal caprolactam salt. Here the prepolymer comprises a reaction mixture of a ring lactam, polyoxyalkyl triamine, polyether diol and diisocyanate.

U.S. Pat. No. 4,569,982 is directed to a process for the production of polyurea elastomers having desirable hard and soft segment structures, which process is characterized in that relatively high molecular weight aliphatic or aromatic polyamines are mixed in substantially equivalent quantities with low molecular weight, solid, finely divided diisocyanates having melting points of >40° C. This invention provides elastomers which have excellent elastic properties over a broad temperature range.

U.S. Pat. No. 4,581,433 discloses an elastomeric polyurethane-urea coating prepared generally by reacting an isocyanate-terminated prepolymer and a diprimary aromatic diamine. These products are especially useful in the coating of mineral building materials which are frequently moist, e.g. the coating of concrete construction, or of brick work. The advantage of the process according to the invention lies in the fact that when coating such moist mineral substrates, highly elastic, homogeneous coatings, i.e. coatings free from blisters, are obtained.

In an article in Polymer Feb.26, 1985, p. 305 there is disclosed a method by which isophorone diisocyanate is allowed to react with hydroxyl containing prepolymers in the preparation of polyurethane elastomers (particularly with hydroxy-terminated polybutadienes) for composite propellant systems.

In U.S. Pat. No. 4,604,445 there is disclosed a prepolymer comprising the reaction product of a polyisocyanate and an effective amount of at least two polyols. The urethane prepolymer has an improved low strain modulus and an improved tensile strength upon cure.

U.S. Pat. No. 4,581,433 describes a coating composition comprising (i) an isocyanate prepolymer based on bis(4-isocyanatocyclohexyl) methane and polyalkylene ether polyols and (ii) at least one aromatic diamine having at least one alkyl substituent in an ortho-position to one amino group and two alkyl substituents in both ortho-positions to the other amino group.

U.S. Pat. No. 4,611,043 describes a coating composition that is the reaction product of (a) an isocyanate terminated prepolymer which comprises the reaction product of isocyanate groups and polyol and (b) dicyclopentenyl alcohol.

In U.S. Pat. No. 4,614,787 there are disclosed wound dressings having a drug dispersed throughout a polyurethane matrix containing (A) an isocyanate terminated prepolymer formed by reaction of isophorone diisocyanate and a glycol and (B) a monomer containing hydroxyl and vinyl groups.

The above mentioned references are related to the synthesis and the use of isocyanate-terminated polyurethane prepared from polyol and polyisocyanate. These prepolymers are used for the synthesis of polymers, especially polyurethanes.

U.S. Pat. No. 4,609,718 teaches the use of an ultraviolet curing liquid coating composition which is produced from (a) an isocyanate-terminated polyurea from diisocyanate and a high molecular weight diamine and (b) an acrylate compound.

It would be an advance in the art to produce amines of high molecular weight which are active; that is, an amine which has no methyl group on the first carbon position. Many of the amines in the art, such as the polyoxyalkylene amines have various uses, but it would be desirable if a way were devised whereby they could be capped by active amines, such as, triethyleneglycol diamine or tetraethyleneglycol diamine. Distinct advantages would be possessed by such molecules. For example, these high molecular weight active amine terminated prepolymers would be useful for fast curing epoxy resins.

SUMMARY OF THE INVENTION

In accordance with the foregoing the present invention encompasses active amines of various molecular weights with urea or urethane linkages in the molecular structures. In the instant invention, there are two ways to synthesize these novel amine products.

Class A

The synthetic method is similar to Class B using a polyol, except polyoxyalkylene diamines are used instead of a polyol. This is represented as follows:

These products are colorless, viscous liquids or solids, and are useful as epoxy curing agents.

DESCRIPTION OF THE PREFERRED EMBODIMENTS

The present invention is directed to the preparation of various molecular weight active amines containing a urea linkage or a urethane and urea linkage and comprises:

Reacting a compound from the group consisting of a polyoxyalkylene amine or a high molecular weight polyol with an isocyanate to form an intermediate adduct and subsequently reacting the intermediate with an active amine from the group consisting of triethyleneglycol diamine and tetraethyleneglycol diamine.

Where the reactant is a polyol, a tin group catalyst is preferably used in the first step to speed up the reaction.

It would be an advance in the art to be able to synthesize high molecular weight active amines from high Equation A

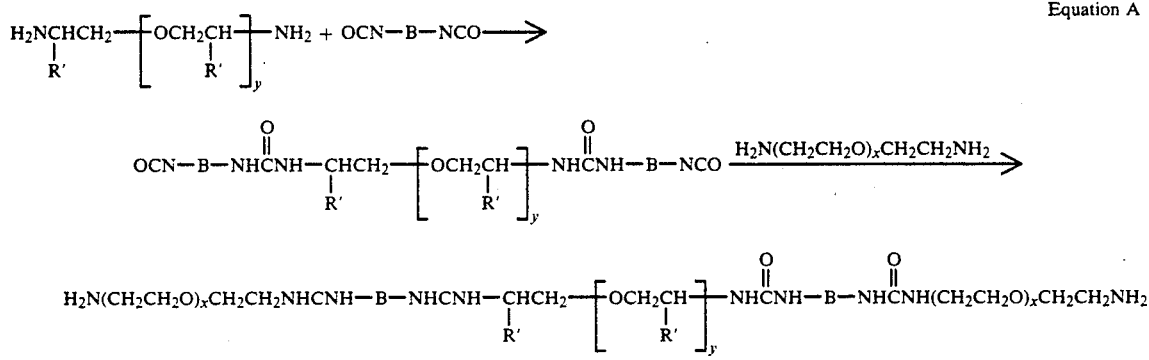

where y = 0 to 60, x = 1 to 3, R' = H or CH$_3$ and
B = nucleus of diisocyanate.

Class B

In the second embodiment the first step involves the preparation of isocyanate-terminated intermediates with a urethane-linkage from polyol and diisocyanate. The second step is to cap the intermediate with active polyoxyethylene diamine. The general structure is described by the following reactions:

molecular weight polyoxyalkyleneamines or polyols and low molecular weight active amines.

One familiar with the art will be aware of difficulties inherent in obtaining a large diamine molecule which possesses the property of being very reactive. Some polyoxyalkylene diamines such as those represented by JEFFAMINE® AMINES (produced by Texaco Chemical Co.) can be produced which have high mo- Equation B

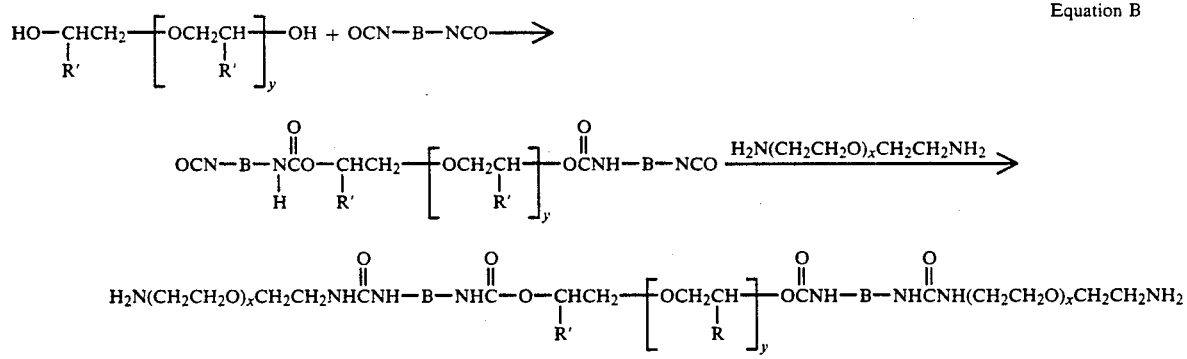

Where y = 0 to 60, x = 1 to 3, R' = H or CH$_3$
B = nucleus of diisocyanate.

The various molecular weight products are prepared by the choice of number y. The active amines are selected by reacting said intermediate adduct with triethyleneglycol diamine (x=2) or tetraethyleneglycol diamine (x=3).

lecular weights, but they are always less active with the amine group attached on a secondary carbon. Certain diamines which have a small molecular weight are characterized as being active. These include triethyleneglycol diamine and tetraethyleneglycol diamine.

There are difficulties in obtaining larger molecular weight active amines. Problems are encountered because of the decomposition of high molecular weight polyoxyethyleneamine during the preparation and the problem of purity. Distillation procedures cannot be used to separate the impurities; therefore the active amines are necessarily smaller molecules.

It has been discovered by the two-step method of this invention that these large polyoxyalkylene molecules can be capped by the active amines to make high molecular weight active amines. Where the reactant is a polyoxyalkyleneamine, a urea linkage is formed.

Where the reactant is a polypropyleneglycol, a urethane and urea linkage is formed. The urea linkage is more stable, however the polyol starting material is cheaper and therefore has obvious advantages.

The Starting Material

In the first embodiment a polyoxyalkylenediamine is reacted with an aliphatic isocyanate to form an intermediate adduct, which is then reacted with an "end" amine to form a colorless product which may be used as an epoxy curing agent.

The polyoxyalkylene polyamine starting materials for the present invention include polyoxypropylene diamines, polyoxyethylene diamines, and polyoxyalkylene diamines containing mixtures of both ethylene oxide and propylene oxide and, preferably, mixtures of from about 5 to about 90 wt % of ethylene oxide with, correspondingly, from about 95 to 10 wt % of propylene oxide. Where mixed propylene oxide/ethylene oxide polyols are employed, the ethylene oxide and propylene oxide may be premixed prior to reaction to form a heterocopolymer, or the ethylene oxide and the propylene oxide may be sequentially added to the ethoxylation kettle to form block oxypropylene/oxyethylene copolymers.

In general, the polyoxyalkylene polyamine starting material may be defined as a polyoxyalkylene polyamine having the formula:

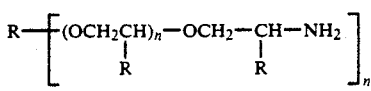

wherein R is the nucleus of an oxyalkylation-susceptible polyhydric alcohol containing 2 to 12 carbon atoms and 2 and 3 hydroxyl groups, and R' is hydrogen or methyl, n is a number having an average value of 0 to 50, and m is an integer having a value of 2 to 3.

In general, the average molecular weight of the polyoxypropylene diamine starting material can be from about 200 to about 5000.

One group of appropriate polyoxyalkylene diamines that may be used are those that are sold by the Texaco Chemical Co. as JEFFAMINE® D-series products having the formula:

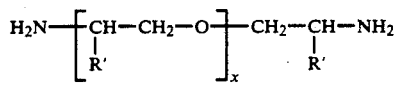

wherein R' independently represents hydrogen or methyl and x is a number having an average value of about 1 to about 60.

Representative products having this structural formula include polyoxypropylene diamines (wherein R' is methyl) having an average molecular weight of about 230 wherein the value of x is between 2 and 3 (JEFFAMINE® D-230 amine), polyoxypropylene diamines having an average molecular weight of about 400 wherein x has a value between about 5 and 6 (JEFFAMINE® D-400 amine), polyoxypropylene diamines having an average molecular weight of about 2000 wherein x has a value of about 33 (JEFFAMINE® D-2000 amine) and a product having an average molecular weight of about 4000 wherein x has a value of about 60 (JEFFAMINE® D-4000 amine).

Where the polyoxyalkyleneamine used is JEFFAMINE® D-2000 the process can be described by Equation I.

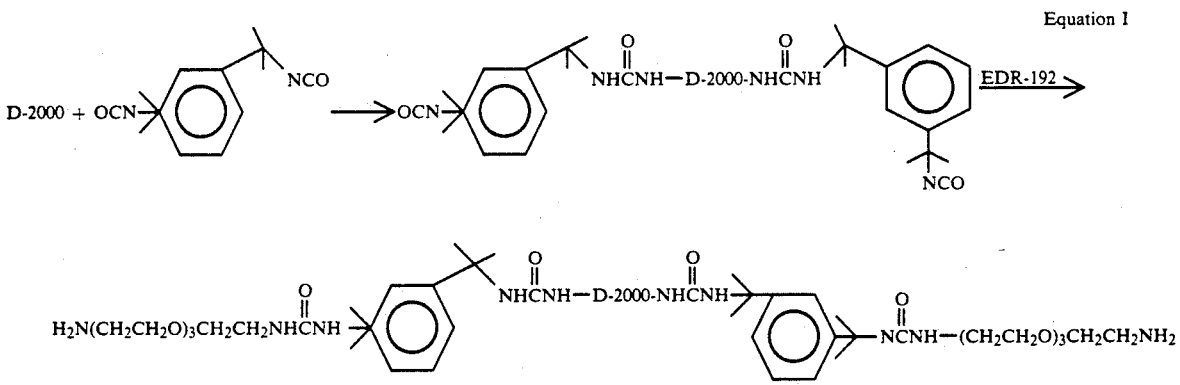

Equation I

Most of these products are light colored, transparent viscous liquids or semisolids. These novel products are to be used as epoxy curing agents and in other polymer applications.

In the embodiment of Class B high molecular weight amines are prepared by reacting a high molecular weight polyol with a diisocyanate and reacting the intermediate product with an "end" or active amine. The products were used as epoxy resin curatives.

Polyols which work well and which are employed in the examples comprise polypropylene glycols having the formula:

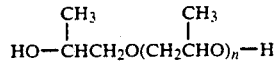

wherein the molecular weight is from 400 to 2000. One commercially available group of polypropylene glycols are JEFFOX® PPG products produced by Texaco Chemical Co.

Polyols which are suitable include polypropylene glycols (such as PPG-400 and PPG-2000) and polyethylene glycols (such as PEG-600).

When the high molecular weight polyol is PPG-2000, the two-step reaction can be represented as follows:

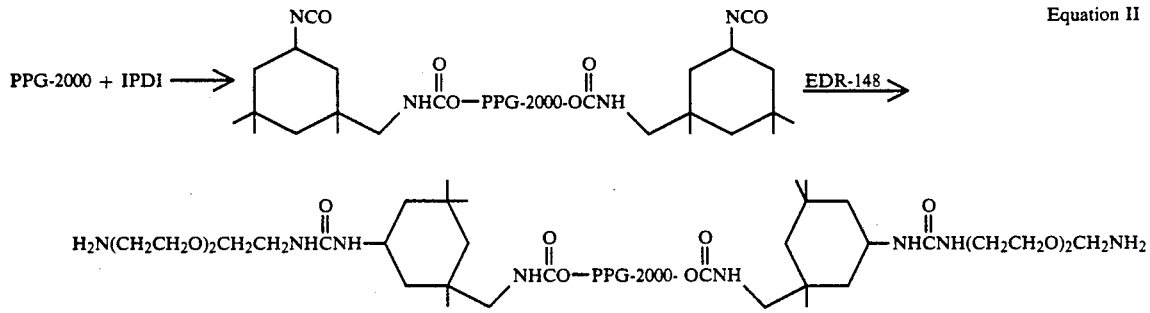

Equation II

The Isocyanate

The isocyanate component for the present invention may be any suitable isocyanate having the desired functionality. Diisocyanates work well in the process. The organic diisocyanate is preferably an aliphatic isocyanate. Although diisocyanates are preferred, other higher polyisocyanates can be used in combination with diisocyanates, or monoisocyanates. Examples of suitable aliphatic diisocyanates are aliphatic diisocyanates such as 1,4-tetramethylene diisocyanate, trimethylhexane diisocyanate, 1,6-hexamethylene diisocyanate, 1,4-cyclohexyl diisocyanate, isophorone diisocyanate, xylylene diisocyanate, m- and p-tetramethylxylylene diisocyanate, 4,4'-methylene-bis(cyclohexyl isocyanate), 2,2,4-trimethylhexamethylene diisocyanate, 2,4,4-trimethylhexamethylene diisocyanate and mixtures thereof. Substituted organic polyisocyanates can also be used in which the substituents are nitro, chloro, alkoxy and other groups which are not reactive with hydroxy groups or active hydrogens, provided the substituents do not adversely affect the intended use of the diamine.

Preferred alkylisocyanates for producing amines containing urea groups include isophorone diisocyanate and tetramethylxylene diisocyanate.

When preparing high molecular weight amines containing urethane and urea linkages the preferred diisocyanates are aliphatic diisocyanates including, but not limited to, tetramethylxylene diisocyanate and isophorone diisocyanate.

Active End Amines

As described above the intermediate adduct of the reaction of the first step is subsequently reacted with an active amine or "end" amine. Suitable amines have the formula:

$$H_2N-(CH_2CH_2-O)_xCH_2CH_2-NH_2$$

where x = 1, 2 or 3.

Suitable active amines that may be used are those sold by Texaco Chemical Co. as JEFFAMINE® EDR-series products, including JEFFAMINE® EDR-148 and JEFFAMINE® EDR-192.

JEFFAMINE® EDR-148 amine is an amine terminated triethylene glycol having the formula:

$$H_2N-CH_2CH_2-O-CH_2CH_2-O-CH_2CH_2-NH_2$$

JEFFAMINE® EDR-192 amine is an amine terminated tetraethyleneglycol having the formula:

$$H_2N-CH_2CH_2-O-CH_2CH_2-O-CH_2CH_2OCH_2CH_2NH_2$$

Other suitable active amines include isophorone diamine dipropylene triamine, and diethylene triamine.

The aforementioned JEFFAMINE® EDR-series amines appear to be very well suited to both the embodiment using a polyoxyalkyleneamine reactant and the embodiment using a polyol.

Solvent

A solvent is critical for carrying out the method of the invention. A solvent is often useful in both steps of the invention for avoiding gel formation. The solvent comprises an alcohol.

Suitable solvents are those which are unreactive toward isocyanate groups. Generally suitable solvents are polar or those having a high dielectric constant. Examples of suitable polar solvents include ethanol, isopropanol, t-butanol and amyl alcohol. Among the solvents studied are methanol, ethanol, i-PrOH and t-BuOH. Good results were obtained using i-prOH or t-BuOH.

Preparation of the Novel Amines

It has been discovered in accordance with the present invention that novel amine products are preferentially formed when an isocyanate is reacted with an excess of polyoxyalkylene diamine or polyol under a nitrogen atmosphere. A temperature within the range of about 0° C. to 75° C. is suitable for the first step using a polyoxyalkylene diamine reactant and about 60°-100° C. in the first step using a polyol reactant. The reaction time is within the range of about 0.1 to about 10 hours for the first step. The second step of the reaction can be run at room temperature and cooling is required to subside exothermic heat. Normally, the reaction will go to completion after a reaction time within the range of about 0.1 to about 4 hours.

In the reaction using a polyol, a catalyst may be used in order to achieve a faster reaction rate. Preferably the catalyst is an organo tin. Tin compounds which can be used include dibutyl tin dioctanoate and dibutyl tin dilaurate. Good results are obtained using dibutyl tin dilaurate.

The first step of the reaction is complete when essentially all amine groups of the polyoxyalkylene diamine have reacted with the isocyanate. Under the noncatalytic reaction conditions the primary amine groups of the polyoxyalkylene diamine are essentially unreactive with each other.

Where a polyol is reacted with an alkyldiisocyanate in the presence of a tin catalyst, the reaction is complete when all hydroxy groups of polyol have reacted with the isocyanate.

The second step is complete when all the isocyanates have reacted with primary amine of polyoxyethylene diamine.

The novel high molecular weight active amines that are formed by the process of the present invention are light colored, transparent, viscous liquids or semisolids having a molecular weight within the range of about 500 to about 6000 and containing at least two urea linkages. Using a polyol reactant, the amine has a molecular weight of about 500-6000 and contains at least two urethane and two urea linkages.

A variety of molecular configurations are possible for the amines of the present invention, depending on the starting materials.

Where the reaction uses JEFFAMINE® D-2000 amine in the first step and JEFFAMINE® EDR-192 amine in the second step. The product can be represented by the structure:

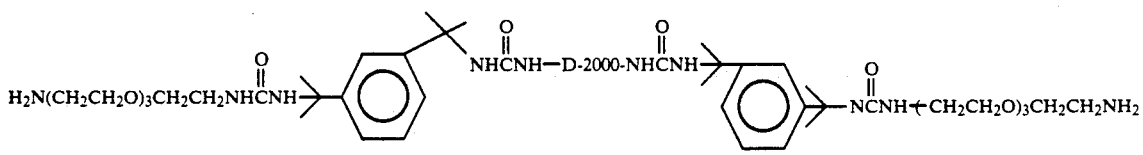

Where a high molecular weight active amine is synthesized by the reaction of a high molecular weight polyol such as JEFFAMINE® PPG-2000 and isophorone diisocyanate and subsequently reacted with JEFFAMINE® EDR-148, amine the product can be represented by the following structure:

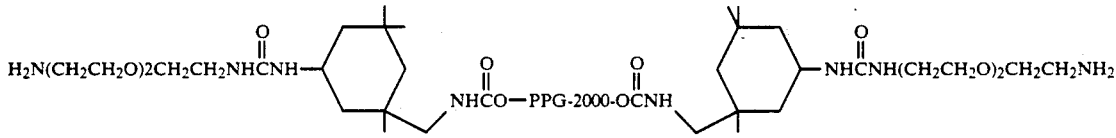

The improvements of this system include the following:
1. Synthesis of a high molecular weight active amine from a high molecular weight PPG or PEG and low molecular weight of amine.
2. Stable urea or urethane linkage
3. In the case of polyoxyalkylene diamine derived prepolymer, no catalyst is needed.

Unexpected advantage of this invention includes:

1. Colorless to slightly colored liquid or semisolid products.

The present invention will be further illustrated by the following examples which are only for the purpose of illustration and are not to be regarded as limiting the invention in any way.

EXAMPLE 1

D-2000-TMXDI-EDR-192 (1:2:2) Adduct

To a 500 ml 3-necked flask equipped with a thermometer, mechanical stirrer, dropping funnel and nitrogen inlet line, was charged tetramethylxylene diisocyanate (TMXDI-meta, American Cyanamid product) (39g, 0;16M). The solution of JEFFAMINE® D-2000 amine (160g, 0.08M) in i-PrOH (160g) was added dropwise through a dropping funnel. The reaction was exothermic, hence the heat was subsided by an ice/water bath to control the pot temperature at 4°-20° C. The addition period lasted for 4 hours. The reaction mixture was poured into another dropping funnel and was added into a solution of JEFFAMINE® EDR-192 amine (31 g, 0.16M) keeping the temperature about 20° C. After standing overnight, the mixture was subjected to a high vacuum and i-PrOH was removed. A white transparent, semisolid product was obtained (249 g). The analysis showed 0.63 meq/g total amine (calc. 0.64).

EXAMPLE 2

-) D-2000-IPDI-EDR-192 (1:2:2) Adduct

The above experimental procedure was repeated except using isophorone diisocyanate as the diisocyanate reactant. The product was viscous, light colored liquid, having analysis of 0.72 meq/g for amine (calc. 0.70).

EXAMPLE 2A (Usage)

The same of Example 2, 34.7 g and Epon 828 (Shell product, 9.4 g) was well mixed and poured into a mold and cured at 90° C. overnight. A very flexible transparent rubbery material was made.

The results in Table I were obtained using the procedures of Example 1.

TABLE I

HIGH MOLECULAR WEIGHT ACTIVE AMINES WITH UREA LINKAGES

| Example No. | Isocyanate Precursors | Terminated Amines | Properties of Products | Total Amine (meq/g) | Calc. |
|---|---|---|---|---|---|
| 1 | D-2000-TMXDI | EDR-192 | Transparent, light | 0.63 | 0.64 |

TABLE I-continued
HIGH MOLECULAR WEIGHT ACTIVE AMINES WITH UREA LINKAGES

| Example No. | Isocyanate Precursors | Terminated Amines | Properties of Products | Total Amine (meq/g) | Calc. |
|---|---|---|---|---|---|
| 2 | D-2000-IPDI | EDR-192 | yellow solid Transparent, light yellow liquid | 0.72 | 0.70 |
| 3 | D-2000-IPDI | EDR-148 | Transparent, light yellow semisolid | 0.68 | 0.73 |
| 4 | D-2000-TMXDI | EDR-148 | Opaque, milky-white liquid | 0.72 | 0.72 |
| 5 | D-2000-IPDI | IPDA | White solid | 0.69 | 0.72 |
| 6 | D-2000-IPDI | DPTA | Transparent, light yellow semisolid | 1.13 0.66 (1°) | 0.74 |
| 7 | D-400-TMXDI | EDR-192 | Transparent, light yellow solid | 1.33 | 1.68 |
| 8 | D-400-IPDI | EDR-192 | Transparent, light yellow solid | 1.63 | 1.63 |

*IPDI: Isophorone diisocyanate
TMXDI: Tetramethylxyxlene diisocyanate
IPDA: Isophorone diamine
DPTA: Dipropylene triamine

EXAMPLE 9

PPG-2000+TMXDI+EDR-148 (1:2:2) Adduct

To a 500 ml 3-necked flask equipped with thermometer, mechanical stirrer, dropping funnel and nitrogen inlet was charged PPG-2000 (200 g, 0.1M, Texaco's product, polypropylene glycol mol. wt. ca. 2000), T-13 (dibutyl tin dilaurate, 0.3 g), and TMXDI (tetramethylxyxlene diisocyanate, American Cyanamid product, 48.8 g, 0.2M). The mixture was heated gently to 75°-100° C. for 3.5 hours, then cooled to ambient temperature. Isopropanol (100 ml) was added to dilute the product mixture. At room temperature, a mixture of EDR-148 (29.6 g, 0.2M) and methanol (100 ml) was added into the flask in one portion. After sitting overnight, the mixture was a homogeneous, colorless liquid. The solvent was removed at 100° C. under reduced pressure. A viscous, light yellow liquid was obtained, having an amine analysis of 0.76 meq/g (calc. 0.72 meq/g).

EXAMPLE 10

PPG-2000+TMXDI+EDR-192 (1:2:2) Adduct

To a one liter 3-necked flask equipped with thermometer, stirrer, dropping funnel and a nitrogen inlet was charged PPG-2000 (200 g, 0.1M), T-13 (0.3 g) and TMXDI (48.8 g, 0.2M). The mixture was heated gently to 60°-80° C. for about 3 hours, then cooled to 0° C. by an ice/water bath. At this temperature, a mixture of EDR-192 (38.4 g, 0.2M and i-PrOH (30 g) was added into the mixture in one portion. A exothermic temperature from 0° C. to 20° C. was observed. The solvent was then stripped under reduced pressure to afford a light yellow liquid product, having an amine analysis of 0.69 meq/g (calc. 0.66 meq/g).

EXAMPLE 10A (Usage)

Usage Example

The product of Example 10 (36.6 g, 725 eq. wt.) and Epon ® 828 (9.4 g, 187 eq. wt.) were mixed and poured into a mold and cured overnight at 88° C. A white, opaque and rubbery material was made.

The results in Table II were obtained using the procedures of Example 9:

TABLE 2
HIGH MOLECULAR WEIGHT OF ACTIVE AMINES WITH URETHANE LINKAGES

| Example No. | Polyol | Isocyanate* | EDR-Amine | Properties of Products NH2meq/g (calc.) |
|---|---|---|---|---|
| 9 | PPG-2000 | TMXDI | EDR-148 | Liquid (vis. light yellow); 0.76 (0.72) |
| 10 | PPG-2000 | TMXDI | EDR-192 | Liquid (light yellow) 0.69 (0.66) |
| 12 | PPG-2000 | IPDI | EDR-148 | Liquid or semisolid (light colored, transparent) 0.73 (0.73) |
| 13 | PPG-2000 | IPDI | EDR-192 | Liquid (light colored transparent) 0.83 (0.71) |
| 14 | PPG-400 | IPDI | EDR-148 | Semisolid (yellow, transparent) 1.79 (1.39) |
| 15 | PPG-400 | IPDI | EDR-192 | Liquid (light yellow, transparent) 2.56 (2.3) |
| 16 | PPG-600 | IPDI | EDR-192 | Liquid (light yellow, transparent) Insol. in H2O; 1.76 (1.44) |

*TMXDI: Meta-tetramethylxylene diisocyanate (from American Cyanamide)
IPDI: Isophorone diisocyanate

What is claimed is:

1. In a two-step method of preparing high molecular weight amines, the improvement of preparing active amines containing urea linkages which comprises reacting a polyoxypropylenediamine of the formula:

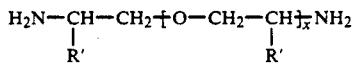

wherein x has a value of 0-60, and R' is methyl with a polyisocyanate selected from the group consisting of isophorone diisocyanate, tetramethylxylene diisocyanate, 1,6-hexamethylene diisocyanate and methylene bis(cyclohexylisocyante), to form an intermediate adduct and subsequently reacting said intermediate adduct with an end amine having the formula:

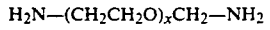

where x=1, 2 or 3, wherein both steps take place without a catalyst.

* * * * *

UNITED STATES PATENT AND TRADEMARK OFFICE
CERTIFICATE OF CORRECTION

PATENT NO. : 5,248,821
DATED : September 28, 1993
INVENTOR(S) : Jiang-Jen Lin, and George Phillip Speranza It is certified that error appears in the above-identified patent and that said Letters Patent is hereby corrected as shown below:

Column 12, line 65, delete "$H_2N-(CH_2CH_2O)_xCH_2-NH_2$" and insert therefor --$H_2N-(CH_2CH_2O)_xCH_2CH_2-NH_2$--.

Signed and Sealed this

Twenty-ninth Day of March, 1994

Attest:

BRUCE LEHMAN

*Attesting Officer*  *Commissioner of Patents and Trademarks*